(12) United States Patent
Tsuchida

(10) Patent No.: US 10,323,049 B2
(45) Date of Patent: Jun. 18, 2019

(54) ORGANOSILICON COMPOUND CONTAINING ISOCYANATE GROUP, PROCESS FOR PRODUCING SAME, ADHESIVE, PRESSURE-SENSITIVE ADHESIVE, AND COATING MATERIAL

(71) Applicant: SHIN-ETSU CHEMICAL CO., LTD., Tokyo (JP)

(72) Inventor: Kazuhiro Tsuchida, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/539,553

(22) PCT Filed: Oct. 5, 2015

(86) PCT No.: PCT/JP2015/078167
§ 371 (c)(1),
(2) Date: Jun. 23, 2017

(87) PCT Pub. No.: WO2016/103836
PCT Pub. Date: Jun. 30, 2016

(65) Prior Publication Data
US 2017/0349614 A1   Dec. 7, 2017

(30) Foreign Application Priority Data
Dec. 24, 2014   (JP) .................................. 2014-260029

(51) Int. Cl.
| | | |
|---|---|---|
| C07F 7/18 | (2006.01) | |
| C09D 183/06 | (2006.01) | |
| C09J 11/06 | (2006.01) | |
| C09J 133/04 | (2006.01) | |
| G02F 1/1335 | (2006.01) | |
| G02B 5/30 | (2006.01) | |

(52) U.S. Cl.
CPC .......... *C07F 7/1892* (2013.01); *C07F 7/1804* (2013.01); *C09D 183/06* (2013.01); *C09J 11/06* (2013.01); *C09J 133/04* (2013.01); *G02B 5/30* (2013.01); *G02F 1/1335* (2013.01)

(58) Field of Classification Search
None
See application file for complete search history.

(56) References Cited

U.S. PATENT DOCUMENTS

| | | | |
|---|---|---|---|
| 3,506,674 A | 4/1970 | Berger et al. | |
| 3,678,089 A | 7/1972 | Berger | |
| 4,654,428 A | 3/1987 | Kurashima et al. | |
| 5,218,133 A | 6/1993 | Pepe et al. | |
| 5,312,690 A | 5/1994 | Fukuda et al. | |
| 5,393,910 A | 2/1995 | Mui et al. | |
| 5,886,205 A | 3/1999 | Uchida et al. | |
| 8,648,162 B2 | 2/2014 | Yasuda et al. | |
| 2011/0151250 A1 | 6/2011 | Yasuda et al. | |
| 2012/0121824 A1 | 5/2012 | Toyama et al. | |

FOREIGN PATENT DOCUMENTS

| | | |
|---|---|---|
| JP | 3-223362 A | 10/1991 |
| JP | 4-223403 A | 8/1992 |
| JP | 5-8713 B2 | 2/1993 |
| JP | 5-8714 B2 | 2/1993 |
| JP | 7-258273 A | 10/1995 |
| JP | 2686420 B2 | 12/1997 |
| JP | 10-1486 A | 1/1998 |
| JP | 2963309 B2 | 10/1999 |
| JP | 3022993 B2 | 3/2000 |
| JP | 3806459 B2 | 8/2006 |
| JP | 2010-275524 A | 12/2010 |
| JP | 2011-137065 A | 7/2011 |
| JP | 4778844 B2 | 9/2011 |
| JP | 2011-219765 A | 11/2011 |
| JP | 4840888 B2 | 12/2011 |
| JP | 2012-197233 A | 10/2012 |
| JP | 5595034 B2 | 9/2014 |
| WO | WO 2010/026995 A1 | 3/2010 |

OTHER PUBLICATIONS

International Search Report issued in PCT/JP2015/078167 (PCT/ISA/210), dated Dec. 15, 2015.
Written Opinion of the International Searching Authority issued in PCT/JP2015/078167 (PCT/ISA/237), dated Dec. 15, 2015.

*Primary Examiner* — Clinton A Brooks
(74) *Attorney, Agent, or Firm* — Birch, Stewart, Kolasch & Birch, LLP

(57) ABSTRACT

The purpose of the present invention is to obtain an organosilicon compound containing an isocyanate group by thiol-ene addition reaction from a corresponding organosilicon compound having a mercapto group and an isocyanate compound having a polymerizable group. Provided is a silane coupling agent which includes a specific linking structure in which a sulfur atom is indispensably contained in a linking chain which connects an isocyanate group to a hydrolyzable silyl group. Compared to silane coupling agents for use in existing technologies, this silane coupling agent has enhanced hydrophobicity and an increased organic-moiety proportion due to the sulfur-containing linking structure. Use of this silane coupling agent as an adhesive modifier hence makes it possible to obtain a pressure-sensitive adhesive in which the silane coupling agent has improved compatibility with the resin and is excellent in terms of strength of bonding to and interaction with the matrix resin having hydroxy groups and which is able to have initial reworkability and further have high adhesive force at high temperatures or under high-temperature high-humidity conditions.

13 Claims, 2 Drawing Sheets

US 10,323,049 B2

Figure 1:
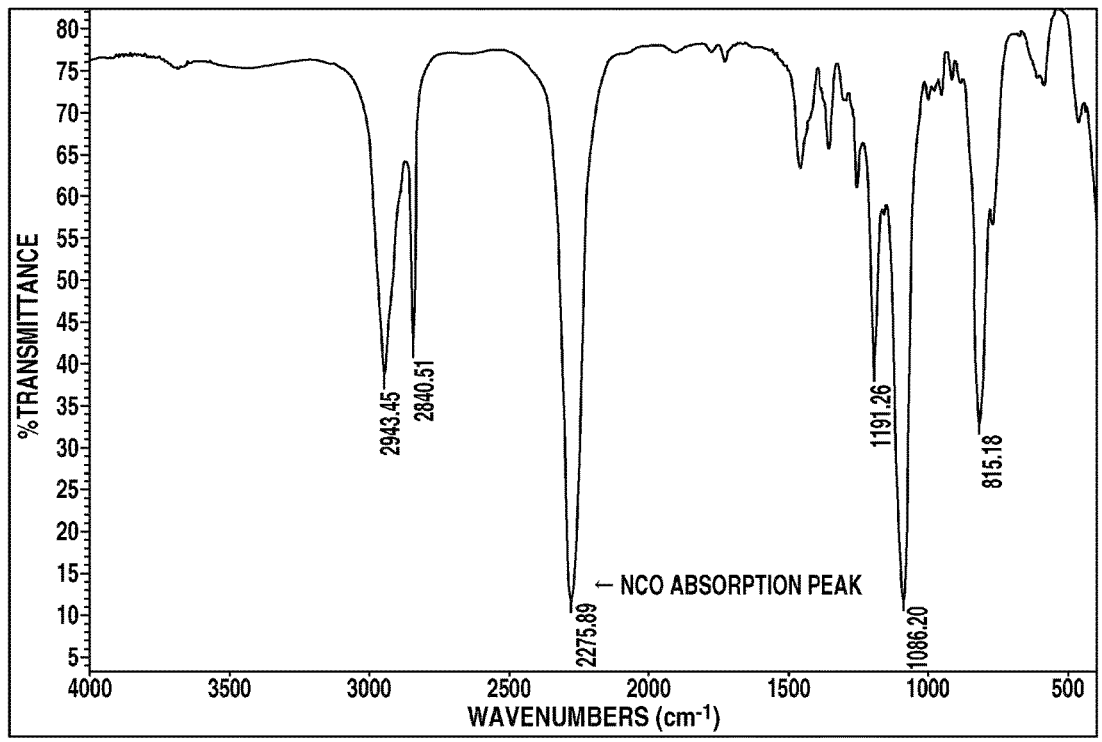

ORGANOSILICON COMPOUND CONTAINING ISOCYANATE GROUP, PROCESS FOR PRODUCING SAME, ADHESIVE, PRESSURE-SENSITIVE ADHESIVE, AND COATING MATERIAL

TECHNICAL FIELD

This invention relates to an isocyanate group-containing organosilicon compound and a method for preparing the same. The invention relates more particularly to an isocyanate group-containing organosilicon compound which invariably includes a sulfur atom on a connecting chain between an isocyanate group and a hydrolyzable silyl group. By using this product as a silane coupling agent, compared with silane coupling agents used in the existing art, the hydrophobicity increases owing to the sulfur-containing connecting structure and organic moieties account for a greater proportion of the molecule. As a result, the compatibility with resins rises and the bonding strength and interaction with matrix resins having hydroxyl groups are excellent, dramatically improving adhesion between matrix resin-containing pressure-sensitive adhesives and substrates. The invention further relates to a method of preparation which is simpler and has better productivity than isocyanatosilane preparation methods disclosed to date. The invention still further relates to a bonding agent, a pressure-sensitive adhesive and a coating agent which use such an isocyanate group-containing organosilicon compound, and additionally relates to articles such as an adhesive polarizer and a liquid-crystal display.

BACKGROUND ART

Silane coupling agents have two or more different functional groups on the molecule and generally function as intermediaries that link together organic materials and inorganic materials which do not readily bond with one another. One of the functional groups is a hydrolyzable silyl group which forms a silanol group in the presence of water. This silanol group reacts with a hydroxyl group on the surface of an inorganic material, forming a chemical bond with the inorganic material surface. The other functional group is an organic reactive group, such as a vinyl, epoxy, amino, (meth)acrylic, mercapto or isocyanate group, which forms a chemical bond with an organic material such as any of various synthetic resins. By virtue of these characteristics, silane coupling agents are widely used as, for example, modifiers for organic and inorganic resins, adhesion promoters, and various types of additives.

Among silane coupling agents, those with isocyanate groups have an excellent reactivity with active hydrogen-containing structural groups such as hydroxyl groups, primary and secondary amino groups and carboxyl groups. Hence, such isocyanate group-containing silane coupling agents are used not only in applications as adhesion-improving agents, but also as resin modifiers for introducing hydrolyzable silyl groups onto organic polymers.

A number of methods for efficiently and industrially preparing isocyanate group-containing organosilicon compounds have been described, including typically methods involving the reaction of an amine with phosgene or the thermal degradation of carbamate. Art relating to the former method is disclosed in, for example, JP-B H05-8713, JP-B H05-8714 and JP No. 3806459 (Patent Documents 1 to 3). However, phosgene is difficult to handle on account of its toxicity, and there remain challenges with this approach in terms of productivity, such as the trapping and removal of hydrochloride generated.

Art relating to the latter method is disclosed in, for example, JP-A H10-1486, JP No. 2686420, JP No. 2963309 and JP No. 4778844 (Patent Documents 4 to 7). Because the toxicity is lower and less by-product is generated than in the phosgene method, this is the mainstream approach for small- and medium-scale isocyanate production. However, this method requires the installation of production equipment that efficiently removes alcohol generated at high temperatures and so, from an industrial perspective, there remain challenges with this approach as well.

A common method known for synthesizing silane coupling agents involves a hydrosilylating reaction between hydrosilane and an olefin compound. An example of this method applied to isocyanatosilane synthesis is hydrosilylation using hydrosilane and a polymerizable group-containing isocyanate. However, allyl isocyanate, which is a typical industrially available polymerizable group-containing isocyanate, has a high toxicity. Moreover, being a nitrogen-containing compound, it poisons the platinum complex that serves as the hydrosilylation reaction catalyst. This reaction thus appears to be impractical.

An organosilicon compound in which there remain unreacted isocyanate groups can be obtained even by reacting one mole of a diisocyanate compound that is readily available industrially with one mole of an organosilicon compound having an active hydrogen-containing structural group, such as an aminosilane or a mercaptosilane. However, given the absence of selectivity here in the reactivity of the isocyanate with the active hydrogen-containing structural group, there are also cases in which some of the starting diisocyanate remains. Also, because side reactions arise in which the NH structures in the urea bonds and thiourethane bonds formed by the reaction react with the remaining isocyanate, it is difficult to obtain the target substance alone. Ensuring the stability of the resulting reaction product also remains a challenge.

Silane coupling agents are typically used also as adhesion modifiers for pressure-sensitive adhesives. In pressure-sensitive adhesives used for attaching liquid crystal cells and optical films, for instance, as the liquid-crystal display (LCD) becomes larger in size and wider, a higher adhesion performance is desired. Contrary to initial expectations that LCD sizes of 20 inches and up would be difficult to achieve, display sizes are rapidly increasing. Major manufacturers have hitherto devoted the bulk of their efforts to the production of small panels less than 20 inches in size. Yet, in line with recent trends, they are now aggressively adopting the latest technology and expanding the range of their products to include large panels 20 inches or more in size.

Thus, in various optical films, the trend in the glass used when manufacturing liquid-crystal display panels is toward larger sizes. However, should a defective product arise during initial attachment, making it necessary to remove the optical film from the liquid-crystal cell and to wash and reuse the cell, in cases where a conventional pressure-sensitive adhesive with a high tack strength has been used, not only would removal of the film be difficult on account of the strong adhesive strength, there would also be a strong likelihood of destroying the expensive liquid-crystal cell during such removal. Hence, this greatly increases the production costs.

Therefore, along with the increase in the size of LCD's, efforts continue to be made to develop high functionality pressure-sensitive adhesives endowed with various adhesive performances such as adhesiveness and reworkability. For example, JP No. 3022993 and JP No. 5595034 (Patent Documents 8 and 9) disclose epoxysilane or isocyanatosilane-containing acrylic pressure-sensitive adhesive compositions, the object being to provide polarizers of excellent durability in high-temperature, high-humidity environments.

Also, JP-A 2011-219765, JP No. 4840888 and WO 2010/26995 (Patent Documents 10 to 12) disclose, as pressure-sensitive adhesives endowed with a low initial adhesive strength, excellent reworkability, increased bonding strength under high temperature and high humidity following attachment, and excellent long-term durability, acrylic pressure-sensitive adhesives which include an organosilicon compound having an alkoxysilyl group on a polyether end.

By including such a silane compound, the substrate and the polarizer can maintain a suitable adhesive strength of the degree required in the actual service environment, the adhesive strength does not rise excessively due to heating and the like, and the polarizer can be easily released without damaging the liquid-crystal element.

Also, in what is a recent technical trend, as touch-sensor LCD's become more widespread, designs that place a pressure-sensitive adhesive layer in direct contact with a transparent electrode layer typically made of indium-tin oxide (ITO) have become the norm. A concern in this product design is that the carboxyl group-containing acrylic polymer base commonly used in pressure-sensitive adhesives may corrode the ITO. Therefore, in its place, a technical transition to pressure-sensitive adhesive compositions based on hydroxyl group-bearing acrylic polymers is underway.

However, in pressure-sensitive adhesives having such an acid-free base polymer composition, the effects obtained using the silane coupling agents that have been effective in conventional pressure-sensitive adhesives are limited; silane coupling agents that help to manifest the same or a higher level of performance have not been found.

Given the above, there exists a desire for a method of preparing isocyanate group-containing organosilicon compounds that is both simple and highly versatile. There is also a desire for, in applications as silane coupling agents, the development of an acid-free base polymer-type pressure-sensitive adhesive which strikes a good balance between the initial reworkability and maintaining a high adhesive strength under high temperature and high humidity.

PRIOR ART DOCUMENTS

Patent Documents

Patent Document 1: JP-B H05-8713
Patent Document 2: JP-B H05-8714
Patent Document 3: JP No. 3806459
Patent Document 4: JP-A H10-1486
Patent Document 5: JP No. 2686420
Patent Document 6: JP No. 2963309
Patent Document 7: JP No. 4778844
Patent Document 8: JP No. 3022993
Patent Document 9: JP No. 5595034
Patent Document 10: JP-A 2011-219765
Patent Document 11: JP No. 4840888
Patent Document 12: WO 2010/26995

SUMMARY OF THE INVENTION

Problems to be Solved by the Invention

In light of the above circumstances, the objects of this invention are to provide a simple and versatile method for preparing isocyanate group-containing organosilicon compounds, an isocyanate group-containing organosilicon compound obtained by such a method, and a bonding agent, a pressure-sensitive adhesive and a coating agent which use such a compound. A further object of the invention is to provide various articles such as glass fiber products, adhesive polarizers and liquid crystal displays.

Pressure-sensitive adhesive compositions containing this organosilicon compound as a silane coupling agent have, during attachment, a low initial adhesive strength and an excellent workability without causing readily corrodible adherends such as ITO films to corrode and, following attachment, have an increased adhesive strength with the adherend after incurring high-temperature or high-temperature, high-humidity treatment and are thus able to provide a pressure-sensitive adhesive layer of excellent long-term durability.

Means for Solving the Problems

The inventor has conducted extensive investigations in order to achieve the above objects. As a result, he has discovered that, by carrying out the thiol-ene addition reaction between a mercapto group-containing organosilicon compound and a polymerizable group-containing isocyanate compound, an organosilicon compounds containing the corresponding isocyanate group can be obtained. The resulting reaction product is a silane coupling agent containing a specific connecting structure that invariably includes a sulfur atom on a connecting chain between an isocyanate group and a hydrolyzable silyl group. By using this silane coupling agent as an adhesion modifier, compared with silane coupling agents used in the existing art, the hydrophobicity increases on account of the sulfur-containing connecting structure, and organic moieties account for a greater proportion of the molecule. As a result, there is obtained a pressure-sensitive adhesive that has an increased compatibility with resins and an excellent bonding strength and interaction with matrix resins having hydroxyl groups, and that is able to achieve both initial reworkability and a high adhesive strength under high-temperature or high-temperature and high-humidity.

Accordingly, this invention provides the following organosilicon compound and method of preparation thereof, the following bonding agent, pressure-sensitive adhesive and coating agent, and the various following articles.

[1] An isocyanate group-containing organosilicon compound characterized by having general formula (1) below

[Chemical Formula 1]

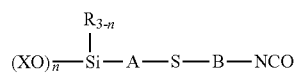

(1)

(wherein X is a monovalent hydrocarbon group of 1 to 4 carbon atoms, R is a monovalent hydrocarbon group of 1 to 6 carbon atoms, A is a divalent hydrocarbon group of 1 to 10 carbon atoms, B is a divalent hydrocarbon group of 2 to 10 carbon atoms that may be bonded through an ester group, and n is an integer from 1 to 3).

[2] The isocyanate group-containing organosilicon compound of [1] which is characterized by having general formula (2) below

[Chemical Formula 2]

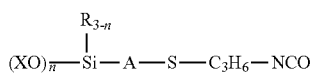
(2)

(wherein X, R, A and n are as defined above).

[3] The isocyanate group-containing organosilicon compound of [1] which is characterized by having general formula (3) below

[Chemical Formula 3]

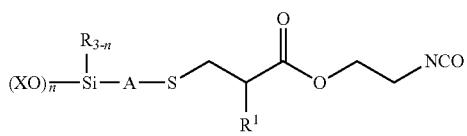
(3)

(wherein X, R, A and n are as defined above, and $R^1$ is a hydrogen atom or a methyl group).

[4] The isocyanate group-containing organosilicon compound of [3] which is characterized in that $R^1$ is a hydrogen atom.

[5] A method for preparing the isocyanate group-containing organosilicon compound of any one of [1] to [4], which method is characterized by comprising the step of thiol-ene addition reacting (i) a mercapto group-containing organosilicon compound of general formula (4) below

[Chemical Formula 4]

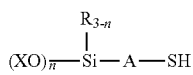
(4)

(wherein X, R, A and n are as defined above) with (ii) an unsaturated double bond-containing isocyanate compound of general formula (5) below

[Chemical Formula 5]

Z—NCO (5)

(wherein Z is an unsaturated double bond-containing monovalent hydrocarbon group of 2 to 10 carbon atoms that may be bonded through an ester group) in the presence of a radical generator.

[6] A bonding agent containing the isocyanate group-containing organosilicon compound of any of [1] to [4].

[7] A pressure-sensitive adhesive containing the isocyanate group-containing organosilicon compound of any of [1] to [4], which pressure-sensitive adhesive is characterized by comprising:
(A) 100 parts by weight of an alcoholic hydroxyl group-containing acrylic polymer,
(B) from 0.001 to 10 parts by weight of the isocyanate group-containing organosilicon compound, and
(C) from 0.01 to 10 parts by weight of a polyfunctional crosslinking agent.

[8] A coating agent containing the isocyanate group-containing organosilicon compound of any of [1] to [4].

[9] An article obtained by coating or surface treating a substrate with the coating agent of [8].

[10] The article of [9], wherein the substrate that is coated or surface-treated with the coating agent is a glass fiber product selected from among glass cloth, glass tape, glass mat and glass paper.

[11] The article of [9], wherein the substrate that is coated or surface-treated with the coating agent is an inorganic filler.

[12] The article of [9], wherein the substrate that is coated or surface-treated with the coating agent is ceramic or metal.

[13] An adhesive polarizer which is characterized by comprising a polarizing film and an adhesive layer formed on one or both sides of the polarizing film using the pressure-sensitive adhesive of [7].

[14] A liquid crystal display which is characterized by including a liquid crystal panel that comprises a liquid crystal cell wherein liquid crystals are sealed between a pair of glass plates and, attached to one or both sides of the liquid crystal cell, the adhesive polarizer of [13].

Advantageous Effects of the Invention

This invention is able to easily obtain an isocyanate group-containing organosilicon compound while using existing industrial starting materials that are readily available. The resulting organosilicon compound contains a specific connecting structure that invariably includes a sulfur atom on a connecting chain between an isocyanate group and a hydrolyzable silyl group. In pressure-sensitive adhesive applications, by including a silane coupling agent as an essential ingredient of an adhesion modifier, it is possible to achieve both initial reworkability and a high adhesive strength at high temperature or high temperature and high humidity.

BRIEF DESCRIPTION OF THE DIAGRAMS

Figure 2:
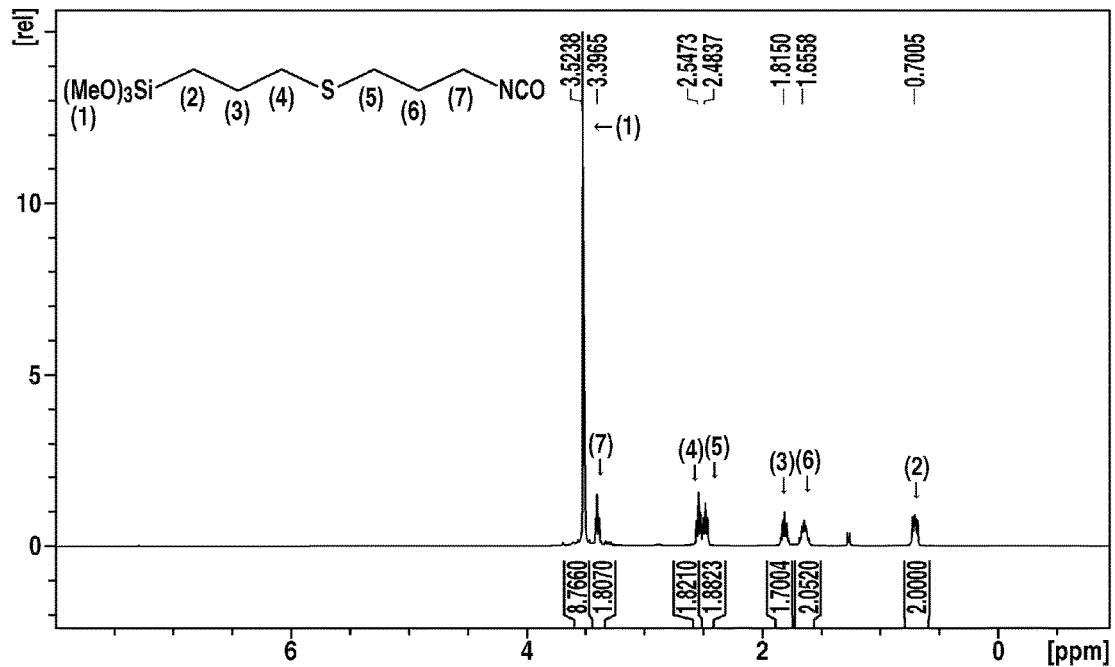
Figure 3:
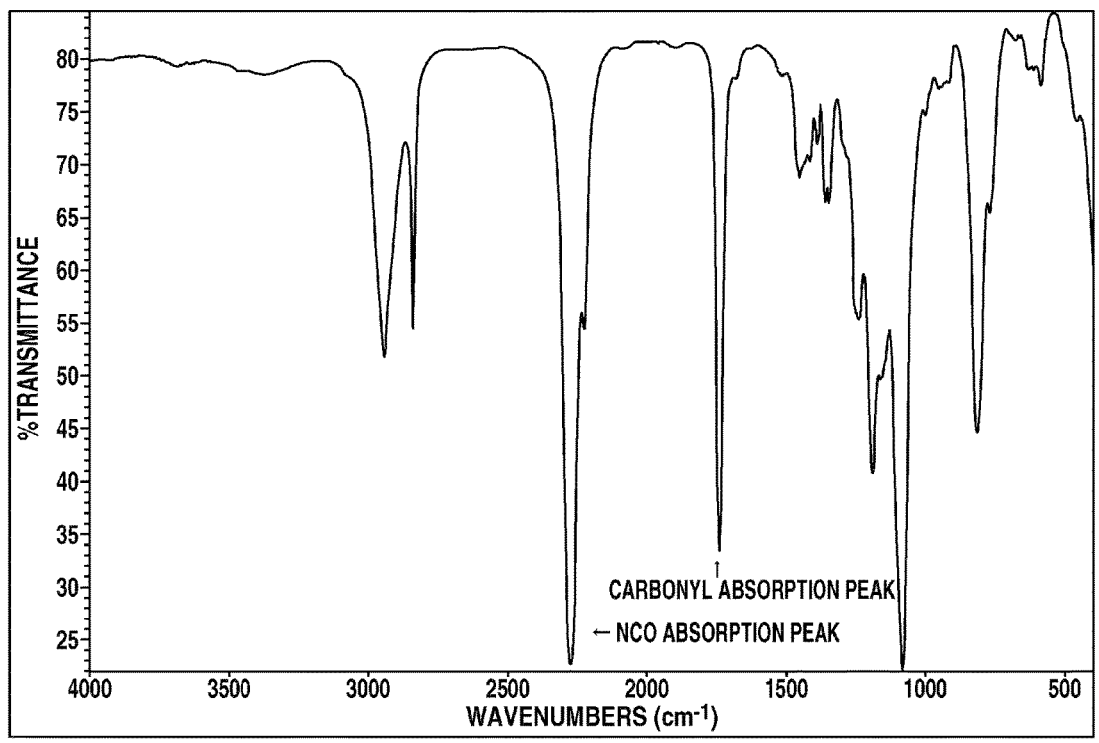
Figure 4:
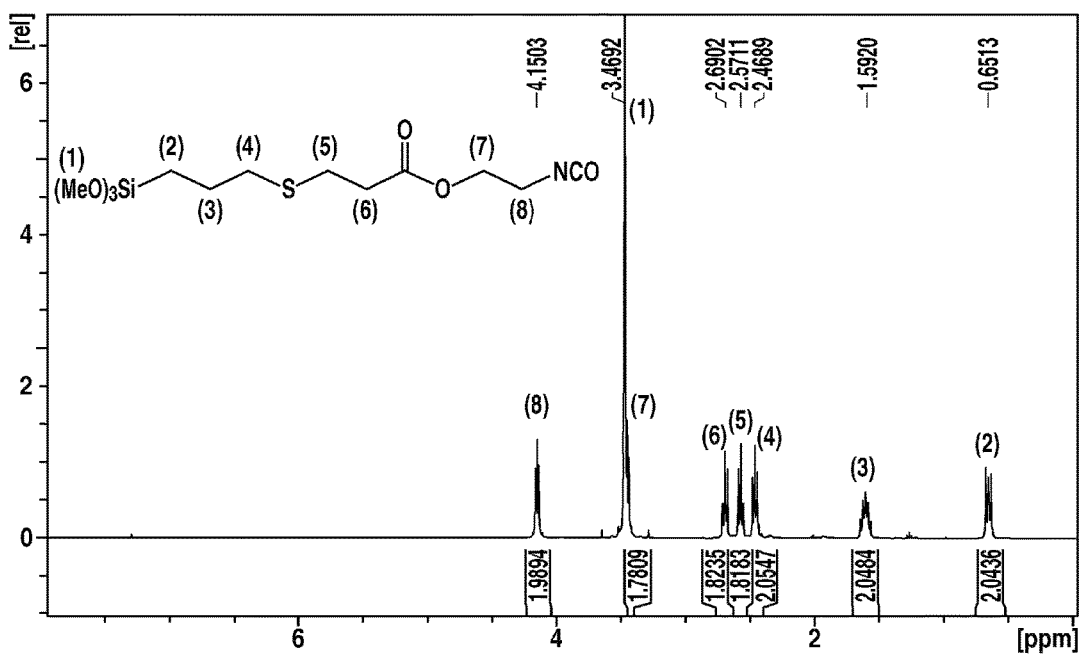

FIG. 1 shows an IR spectrum of the reaction product obtained in Working Example 1.
FIG. 2 shows a $^1$H-NMR spectrum of the reaction product obtained in Working Example 1.
FIG. 3 shows an IR spectrum of the reaction product obtained in Working Example 7.
FIG. 4 shows a $^1$H-NMR spectrum of the reaction product obtained in Working Example 7.

EMBODIMENT FOR CARRYING OUT THE INVENTION

The invention is described more fully below. In this invention, "silane coupling agent" is encompassed by the term "organosilicon compound."

[Organosilicon Compound (Silane Coupling Agent)]

The isocyanate group-containing organosilicon compound of the invention has general formula (1) below.

[Chemical Formula 6]

(1)

In the formula, X is a monovalent hydrocarbon group of 1 to 4 carbon atoms, R is a monovalent hydrocarbon group of 1 to 6 carbon atoms, A is a divalent hydrocarbon group of 1 to 10 carbon atoms, B is a divalent hydrocarbon group of 2 to 10 carbon atoms that may be bonded through an ester group, and n is an integer from 1 to 3.

The compound more preferably has general formula (2) below

[Chemical Formula 7]

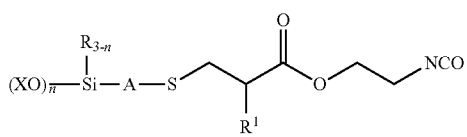
(2)

(wherein X, R, A and n are as defined above) or general formula (3) below

[Chemical Formula 8]

(3)

$$\underset{\text{(XO)}_n}{\overset{R_{3-n}}{\text{Si}}}-A-S\diagdown\underset{R^1}{\overset{O}{\diagup}}\diagdown O\diagdown NCO$$

(wherein X, R, A and n are as defined above, and $R^1$ is a hydrogen atom or a methyl group).

In the case of formula (3), from the standpoint of the production efficiency during the subsequently described preparation, $R^1$ is preferably a hydrogen atom.

Illustrative examples of the monovalent hydrocarbon group of 1 to 4 carbon atoms represented above by X include alkyl groups such as methyl, ethyl, propyl and butyl groups, with methyl and ethyl groups being preferred. This is because the subsequently described mercapto group-containing silane coupling agents that serve as a reaction starting material are readily available.

Illustrative examples of the monovalent hydrocarbon group of 1 to 6 carbon atoms represented above by R include alkyl groups such as methyl, ethyl, propyl, butyl, pentyl and hexyl groups, and also the phenyl group. The alkyl group may be acyclic, branched or cyclic. A methyl group is preferred. This is because the subsequently described mercapto group-containing silane coupling agents that serve as a reaction starting material are readily available.

Illustrative examples of the divalent hydrocarbon group of 1 to 10 carbon atoms represented above by A include alkylene groups such as methylene, ethylene, propylene, butylene, pentylene, hexylene, heptylene, octylene, nonylene and decylene groups. These may be acyclic, branched or cyclic. Propylene, hexylene and octylene groups are preferred, with a propylene group being more preferred. This is because the subsequently described mercapto group-containing silane coupling agents that serve as a reaction starting material are readily available.

Of the divalent hydrocarbon group of 2 to 10 carbon atoms that may be bonded through an ester group and is represented above by B, illustrative examples of divalent hydrocarbon groups of 2 to 10 carbon atoms that are not bonded through an ester group include alkylene groups such as ethylene, propylene, butylene, pentylene, hexylene, heptylene, octylene, nonylene and decylene groups. These may be acyclic, branched or cyclic. Illustrative examples of divalent hydrocarbon groups of 2 to 10 carbon atoms that are bonded through an ester group include 3-one-4-oxahexane-1,6-diyl, 2-methyl-3-one-4-oxahexane-1,6-diyl, 3-one-4-oxaoctane-1,8-diyl, 2-methyl-3-one-4-oxaoctane-1,8-diyl, 3-one-4-oxadecane-1,10-diyl and 2-methyl-3-one-4-oxadecane-1,10-diyl groups. Preferred examples include methylene, propylene, hexylene, octylene, 3-one-4-oxahexane-1,6-diyl and 2-methyl-3-one-4-oxahexane-1,6-diyl groups. More preferred examples include propylene, 3-one-4-oxahexane-1,6-diyl and 2-methyl-3-one-4-oxahexane-1,6-diyl groups. This is because the subsequently described unsaturated hydrocarbon double bond structural group-containing isocyanate compounds that serve as a reaction starting material are readily available.

Examples of isocyanate group-containing organosilicon compounds having more specific structures than above include, but are not limited to, the following group of compounds.

[Chemical Formula 9]

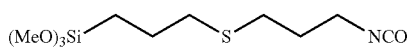
(6)

[Chemical Formula 10]

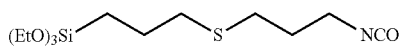
(7)

[Chemical Formula 11]

(8)

[Chemical Formula 12]

(9)

[Chemical Formula 13]

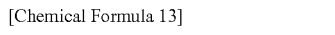
(10)

[Chemical Formula 14]

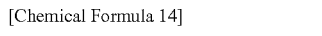
(11)

[Chemical Formula 15]

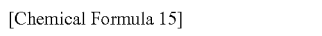
(12)

[Chemical Formula 16]

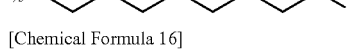
(13)

[Chemical Formula 17]

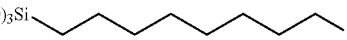
(14)

[Chemical Formula 18]

(15)

-continued

[Chemical Formula 19]

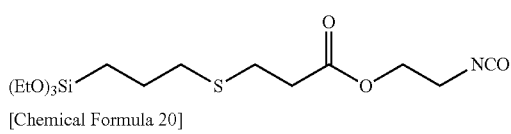
(16)

[Chemical Formula 20]

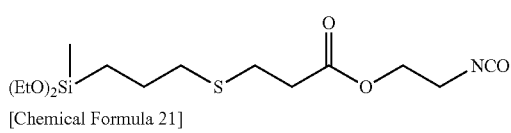
(17)

[Chemical Formula 21]

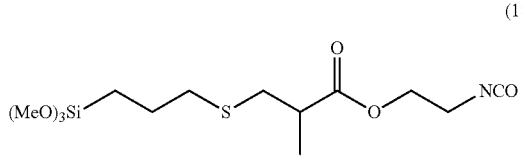
(18)

[Chemical Formula 22]

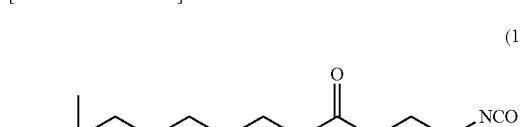
(19)

[Chemical Formula 23]

(20)

[Chemical Formula 24]

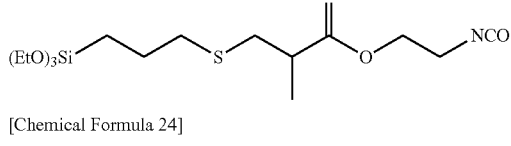
(21)

[Chemical Formula 25]

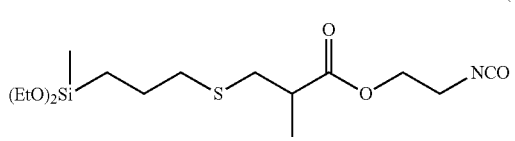
(22)

[Chemical Formula 26]

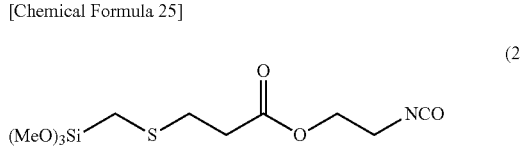
(23)

[Chemical Formula 27]

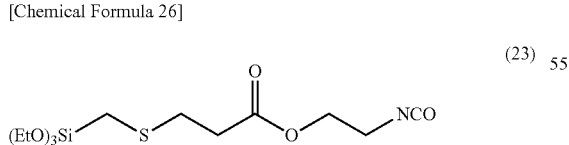
(24)

[Chemical Formula 28]

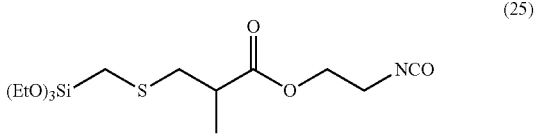
(25)

[Chemical Formula 29]

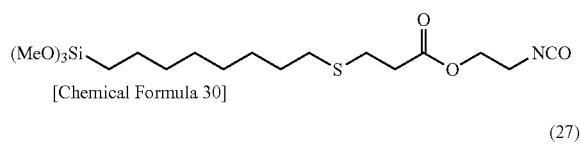
(26)

[Chemical Formula 30]

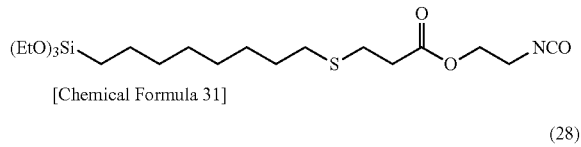
(27)

[Chemical Formula 31]

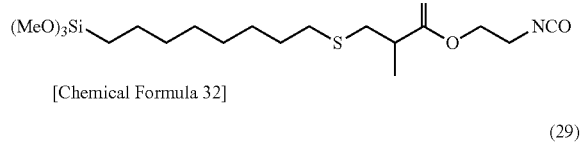
(28)

[Chemical Formula 32]

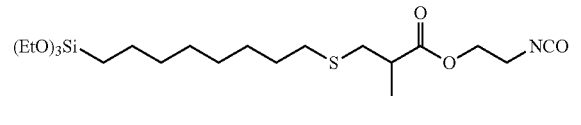
(29)

In the above formulas, "Me" stands for a methyl group and "Et" stands for an ethyl group.

The isocyanate group-containing organosilicon compound of the invention is synthesized by ene-thiol addition-reacting
(i) a mercapto group-containing organosilicon compound of general formula (4) below

[Chemical Formula 33]

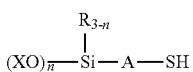
(4)

(wherein X, R, A and n are as defined above) with
(ii) an unsaturated double bond-containing isocyanate compound of general formula (5) below

[Chemical Formula 34]

Z—NCO (5)

(wherein Z is an unsaturated double bond-containing monovalent hydrocarbon group of 2 to 10 carbon atoms that may be bonded through an ester group) in the presence of a radical generator.

More specifically, a mercapto group and a carbon-carbon double bond are addition-reacted to form a thioether bond according to a reaction scheme like that shown below, thereby obtaining a silane coupling agent that includes a hydrolyzable silyl group and an isocyanate structure.

[Chemical Formula 35]

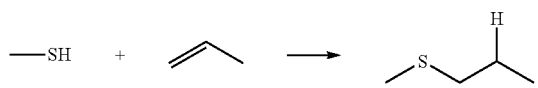

R, A, X and n in the mercapto group-containing organosilicon compound used in this reaction are as defined above. Of these, examples of readily available compounds include mercaptopropyltrimethoxysilane, mercaptopropylmethyldimethoxysilane, mercaptopropyldimethylmethoxysilane, mercaptopropyltriethoxysilane, mercaptopropylmethyldiethoxysilane, mercaptopropyldimethylethoxysilane, mercaptomethyltrimethoxy silane, mercaptomethylmethyldimethoxysilane, mercaptomethyldimethylmethoxysilane, mercaptomethyltriethoxysilane, mercaptomethylmethyldiethoxysilane, mercaptomethyldimethylethoxysilane, mercaptooctyltrimethoxysilane, mercaptooctylmethyldimethoxy silane, mercaptooctyldimethylmethoxysilane, mercaptooctyltriethoxysilane, mercaptooctylmethyldiethoxysilane and mercaptooctyldimethylethoxysilane. Mercaptopropyltrimethoxysilane and mercaptopropyltriethoxysilane, which are more readily available industrially, are preferred.

Examples of the unsaturated hydrocarbon double bond structural group-containing isocyanate compound used in the invention that are more readily available include allyl isocyanate, 2-isocyanatoethyl acrylate and 2-isocyanotoethyl methacrylate. Of these, from the standpoint of toxicity, 2-isocyanatoethyl acrylate and 2-isocyanatoethyl methacrylate, which have a low toxicity and are easy to handle, are preferred. 2-Isocyanatoethyl acrylate, which has a good thiol-ene reactivity, is most preferred.

With regard to the reaction ratio between the above mercapto group-containing organosilicon compound and the unsaturated hydrocarbon double bond structural group-containing isocyanate compound, the reaction is preferably effected at an amount of the mercapto group-containing organosilicon compound of from 0.9 to 1.1 moles, and especially from 0.95 to 1.05 moles, per mole of the unsaturated hydrocarbon double bond structural group-containing isocyanate compound.

The radical generator used in this reaction is exemplified by thermal radical generators and photoradical generators, with thermal radical generators such as azo compounds and peroxides being preferred.

Illustrative examples of thermal radical generators include organic peroxides such as dialkyl peroxides (e.g., di-t-butyl peroxide, dicumyl peroxide), diacyl peroxides [e.g., dialkanoyl peroxides (lauroyl peroxide, etc.), diaroyl peroxides (benzoyl peroxide, benzoyl toluyl peroxide, toluyl peroxide, etc.)], peracid esters [e.g., alkyl esters of percarboxylic acids, such as t-butyl peracetate, t-butyl peroxyoctoate and t-butyl peroxybenzoate], ketone peroxides, peroxycarbonates and peroxyketals; and azo compounds such as azonitrile compounds [e.g., 2,2'-azobis(2,4-dimethylvaleronitrile), 2,2'-azobis(isobutyronitrile), 2,2'-azobis(2-methylbutyronitrile) and 2,2'-azobis(4-methoxy-2,4-dimethylvaleronitrile)], azoamide compounds {e.g., 2,2'-azobis{2-methyl-N-[1,1-bis(hydroxymethyl)-2-hydroxyethyl]propionamide}, azoamidine compounds {e.g., 2,2'-azobis(2-amidinopropane) dihydrochloride and 2,2'-azobis[2-(2-imidazolin-2-yl)propane]dihydrochloride}, azoalkane compounds [e.g., 2,2'-azobis(2,4,4-trimethylpentane) and 4,4'-azobis(4-cyanopentanoic acid)], and azo compounds having an oxime skeleton [e.g., 2,2'-azobis(2-methylpropionamide oxime)]. The thermal radical generator may be used singly or two or more may be used in combination.

Illustrative examples of photoradical generators include benzoins (e.g., benzoin and benzoin alkyl ethers such as benzoin methyl ether, benzoin ethyl ether, benzoin isopropyl ether and benzoin isobutyl ether); acetophenones (e.g., acetophenone, p-dimethylacetophenone, 2-hydroxy-2-methyl-1-phenylpropan-1-one, 2,2-diethoxyacetophenone, 2,2-dimethoxy-2-phenylacetophenone, 2,2-diethoxy-2-phenylacetophenone, 2-phenyl-2-hydroxyacetophenone, 1,1-dichloroacetophenone and 1-hydroxycyclohexyl phenyl ketone); propiophenones (e.g., p-dimethylaminopropiophenone, 2-hydroxy-2-methylpropiophenone and 2,2-dimethoxy-1,2-diphenylethan-1-one); butyrylphenones [e.g., 1-[4-(2-hydroxyethoxy)phenyl]-2-hydroxy-2-methyl-1-propan-1-one, 2-hydroxy-2-methyl-1-phenylpropan-1-one and 1-(4-isopropylphenyl)-2-hydroxy-2-methylpropan-1-one]; aminoacetophenones [e.g., 2-methyl-2-morpholino(4-thiomethylphenyl)propan-1-one, 2-methyl-1-[4-(methylthio)phenyl]-2-morpholinopropan-1-one, 2-benzyl-2-dimethylamino-1-(4-morpholinophenyl)-butan-1-one, 2-dimethylamino-2-methyl-1-phenylpropan-1-one, 2-diethylamino-2-methyl-1-phenylpropan-1-one, 2-methyl-2-morpholino-1-phenylpropan-1-one, 2-dimethylamino-2-methyl-1-(4-methylphenyl)propan-1-one, 1-(4-butylphenyl)-2-dimethylamino-2-methylpropan-1-one, 2-dimethylamino-1-(4-methoxyphenyl)-2-methylpropan-1-one, 2-dimethylamino-2-methyl-1-(4-methylthiophenyl)propan-1-one and 2-benzyl-2-dimethylamino-1-(4-dimethylaminophenyl)-butan-1-one]; benzophenones (e.g., benzophenone, benzil, and N,N-dialkylaminobenzophenones such as N,N'-bis(dimethylamino)benzophenone (Michler's ketone) and 3,3-dimethyl-4-methoxybenzophenone); ketals (e.g., acetophenone dimethyl ketal and benzyl dimethyl ketal); thioxanthenes (e.g., thioxanthene, 2-chlorothioxanthene and 2,4-diethylthioxanthene); anthraquinones (e.g., 2-ethylanthraquinone, 1-chloroanthraquinone, 1,2-benzanthraquinone and 2,3-diphenylanthraquinone); (thio)xanthones (e.g., thioxanthone, 2,4-dimethylthioxanthone, 2,4-diethylthioxanthone, 2-chlorothioxanthone and 2,4-diisopropylthioxanthone); acridines (e.g., 1,3-bis-(9-acridinyl)propane, 1,7-bis-(9-acridinyl)heptane and 1,5-bis-(9-acridinyl)pentane); triazines (e.g., 2,4,6-tris(trichloromethyl)-s-triazine, 2-(4-methoxyphenyl)-4,6-bis(trichloromethyl)-s-triazine and 2,4-bis-trichloromethyl-6-(3-bromo-4-methoxy)styrylphenyl-s-triazine); sulfides (e.g., benzyl diphenyl sulfide); acylphosphine oxides (e.g., 2,4,6-trimethylbenzoyl diphenylphosphine oxide); titanocenes; and oxime esters. These photoradical generators may be used singly or two or more may be used in combination.

The amount of radical generator used per 100 parts by weight of the total amount of mercapto group-containing organosilicon compound and unsaturated hydrocarbon double bond structural group-containing isocyanate compound may be selected from the range of 0.01 to 15 parts by weight, and preferably 0.1 to 10 parts by weight.

The reaction temperature is preferably from 25 to 120° C., and more preferably from 60 to 100° C. At a temperature below 25° C., the reaction rate may fall, whereas at above 120° C., there is a possibility of side-reactions such as polymerization between olefin compounds arising. The reaction time is not particularly limited, but is generally from 10 minutes to 24 hours.

This reaction is characterized in that the reaction is effected by the dropwise addition of the unsaturated hydrocarbon double bond structural group-containing isocyanate compound in the presence of a mercapto group-containing organosilicon compound and a radical generator. Reversing the starting materials that are charged and added dropwise merely gives rise to homopolymerization of the unsaturated hydrocarbon double bond structural unit-containing isocyanate compound; the target compound is not obtained.

A solvent may be used when carrying out the reaction. Use can be made of any solvent that does not react with mercapto groups, isocyanate groups and unsaturated carbon-carbon double bonds. Exemplary solvents include hydrocarbon solvents, aromatic solvents, ketone solvents, ester solvents and ether solvents. Illustrative examples of hydrocarbon solvents include pentane, hexane, heptane, octane, decane and cyclohexane. Illustrative examples of aromatic solvents include benzene, toluene and xylene. Illustrative examples of ketone solvents include acetone, methyl ethyl ketone, methyl isobutyl ketone and cyclohexanone. Illustrative examples of ester solvents include ethyl acetate, butyl acetate and lactone. Illustrative examples of ether solvents include diethyl ether, dibutyl ether, cyclopentyl methyl ether, tetrahydrofuran and 1,4-dioxane. Of these, solvents that are readily available industrially, such as toluene and xylene, are preferred.

When the isocyanate group-containing organosilicon compound of the invention is used as a coating agent or a primer, a solvent may be optionally included. In such cases, the content of the isocyanate group-containing organosilicon compound is preferably from 0.1 to 90 wt %, and especially from 1 to 50 wt %, of the total, with the balance being the solvent used as an optional ingredient. The solvent may be the same as the above-mentioned reaction solvent.

Inorganic materials that react with hydrolyzable silyl groups to form bonds and organic resins that bond by reacting with isocyanate groups may generally be employed as the substrate to be coated and treated. The shape of the substrate is not particularly specified. Of these, examples of typical inorganic materials include inorganic fillers such as silica; glass fibers as well as glass fiber products such as glass cloth, glass tape, glass mat and glass paper; and also ceramic substrates and metal substrates. Examples of typical organic resins include, but are not limited to, polyethers, polyvinyl alcohols, hydroxyl group-containing acrylic resins, epoxy resins, phenolic resins, polyimide resins and unsaturated polyester resins.

Next, a pressure-sensitive adhesive containing the isocyanate group-containing organosilicon compound of the invention is described. This pressure-sensitive adhesive preferably includes:
(A) 100 parts by weight of an alcoholic hydroxyl group-containing acrylic polymer ((meth)acrylic copolymer),
(B) from 0.001 to 10 parts by weight of the above isocyanate group-containing organosilicon compound, and
(C) from 0.01 to 10 parts by weight of a polyfunctional crosslinking agent.

Hence, a pressure-sensitive adhesive containing the isocyanate group-containing organosilicon compound of the invention includes preferably from 0.001 to 10 parts by weight, and more preferably from 0.01 to 1 part by weight, of (B) an isocyanate group-containing organosilicon compound per 100 parts by weight of (A) an alcoholic hydroxyl group-containing acrylic polymer. At less than 0.001 part by weight, the desired adhesion-modifying effect does not appear, whereas at more than 10 parts by weight, this effect increases no further and the cost-effectiveness decreases, in addition to which the influence of the adhesion-enhancing effect inherent to the silane coupling agent becomes large, which may have the undesirable effect of resulting in too large an initial adhesiveness.

Here, the alcoholic hydroxyl group-containing acrylic polymer is exemplified by copolymers of an alcoholic hydroxyl group-containing (meth)acrylic monomer with an alkyl (meth)acrylate monomer, and can be prepared using a known copolymerization procedure. The alcoholic hydroxyl group-containing (meth)acrylic monomer may be one that is available as a common industrial product, and is exemplified by hydroxyethyl (meth)acrylates and hydroxybutyl (meth) acrylates. The alkyl (meth)acrylate is similarly available as an ordinary industrial product, and is exemplified by those in which the alkyl group is a methyl, ethyl, propyl or butyl group. The content of alcoholic hydroxyl group-containing (meth)acrylic monomer units with respect to the total monomer units in the copolymer may be in the range of from 0.1 to 50 mol %, and preferably from 1 to 20 mol %. At less than 0.1 mol %, the desired tackiness may not be obtained, whereas at more than 50 mol %, formation into an adhesive sheet or the like may be difficult due to increased viscosity or agglomeration of the pressure-sensitive adhesive.

Component (C) in the pressure-sensitive adhesive of the invention is a polyfunctional crosslinking agent. The polyfunctional crosslinking agent serving as component (C) has the role of increasing the cohesion of the pressure-sensitive adhesive due to reaction with carboxyl groups, hydroxyl groups or the like. The crosslinking agent is used in an amount of from 0.01 to 10 parts by weight, and preferably from 0.05 to 5 parts by weight, per 100 parts by weight of component (A). At less than 0.01 part by weight, the desired cohesion-enhancing effect may not be obtained, whereas an amount of more than 10 parts by weight triggers agglomeration, which may make formation into an adhesive sheet or the like difficult.

The polyfunctional crosslinking agent may be, for example, an isocyanate, epoxy, aziridine or metal chelate-type crosslinking agent. Of these, an isocyanate crosslinking agent is easy to use. Illustrative examples of isocyanate crosslinking agents include tolylene diisocyanate, xylene diisocyanate, diphenylmethane diisocyanate, hexamethylene diisocyanate, isophorone diisocyanate, tetramethylxylene diisocyanate, naphthalene diisocyanate, and reaction products of these with a polyol such as trimethylolpropane (e.g., the addition product of trimethylolpropane and tolylene diisocyanate).

Illustrative examples of epoxy crosslinking agents include ethylene glycol diglycidyl ether, trimethylolpropane triglycidyl ether, N,N,N',N'-tetraglycidyl ethylenediamine, glycerol diglycidyl ether, glycerol triglycidyl ether, polyglycerol polyglycidyl ether and sorbitol-type polyglycidyl ethers.

Illustrative examples of aziridine crosslinking agents include N,N'-toluene-2,4-bis(1-aziridine carboxide), N,N'-diphenylmethane-4,4'-bis(1-aziridine carboxide), triethylene melamine, bisisophthaloyl-1-(2-methylaziridine) and tri-1-aziridinylphosphinoxide.

Illustrative examples of metal chelate-type crosslinking agents include compounds in which a polyvalent metal such as aluminum, iron, zinc, tin, titanium, antimony, magnesium or vanadium is coordinated with acetylacetone or ethyl acetoacetate.

The method for producing the pressure-sensitive adhesive is not particularly limited. The pressure-sensitive adhesive may be obtained by mixing together above components (A) to (C) in the usual manner. The mixing conditions are preferably set to 10 minutes to 10 hours of mixing at from 10 to 150° C. The isocyanate group-containing organosilicon compound may be used here by addition in a compounding step following polymerization of the (meth)acrylic copolymer, although the same effects are exhibited even when it is added during the (meth)acrylic copolymer production step. As for the polyfunctional crosslinking agent, uniform coating is possible when crosslinking reactions by the functional groups on the crosslinking agent substantially do not arise in the compounding step carried out for the purpose of forming a pressure-sensitive agent layer obtainable by curing the pressure-sensitive adhesive composition. A crosslinked structure is formed via drying and aging steps after coating, enabling a pressure-sensitive adhesive layer that has flexibility and strong cohesion to be obtained.

By applying the pressure-sensitive adhesive thus obtained onto an adherend such as a glass plate, plastic film or paper, and curing for 5 minutes to 5 hours at 25 to 150° C. and 20 to 90% RH, and especially for 10 minutes to 3 hours at 40 to 80° C. and 25 to 60% RH, a pressure-sensitive adhesive layer can be formed.

An adhesive polarizer which includes a pressure-sensitive adhesive layer formed by applying the pressure-sensitive adhesive onto one or both sides of a polarizing film and curing the applied adhesive has a polarizing film or polarizing element and a pressure-sensitive adhesive layer formed of the pressure-sensitive adhesive on one or both sides of the polarizing film or polarizing element. The polarizing film or polarizing element making up the polarizer is not particularly limited. The polarizing film is exemplified by films obtained by incorporating a polarizing ingredient such as iodine or a heterochromatic dye into a film made of polyvinyl alcohol-type resin and stretching the film. These polarizing films are not limited as to their thickness, and may be formed to the customary thickness.

Polyvinyl alcohol, polyvinyl formal, polyvinyl acetal, and saponification products of ethylene-vinyl acetate copolymers and the like may be used as the polyvinyl alcohol-type resin.

Alternatively, it is possible to form a multilayer film obtained by laminating a protective film such as a triacetyl cellulose or other cellulose film, a polycarbonate film, a polyester film such as a polyethylene terephthalate film, a polyethersulfone film, or a polyolefin film made of polyethylene, polypropylene or a copolymer of these onto both sides of a polarizing film having a pressure-sensitive adhesive layer. These protective films have a thickness that is also not particularly limited, and may be formed to the customary thickness.

The method of forming a pressure-sensitive adhesive layer on a polarizing film is not particularly limited. For example, the method employed may be one in which the pressure-sensitive adhesive is applied directly onto the surface of this polarizing film with a bar coater or the like and dried, or may be one in which the pressure-sensitive adhesive is first applied onto the surface of a peelable substrate and dried, following which the pressure-sensitive adhesive layer formed on this peelable substrate surface is transferred to the surface of a polarizing film and subsequently aged. In this case, drying is preferably carried out for 5 minutes to 5 hours at 25 to 150° C. and 20 to 90% RH, and aging is preferably carried out for 5 minutes to 5 hours at 25 to 150° C. and 20 to 90% RH.

The thickness of the pressure-sensitive adhesive layer, although not particularly limited, is preferably from 0.01 to 100 μm, and more preferably from 0.1 to 50 μm. At a thickness smaller than this range, the advantageous effects as a pressure-sensitive adhesive layer may be inadequate. On the other hand, at a thickness larger than this range, the advantageous effects of the pressure-sensitive adhesive layer increase no further and the costs may rise.

One or more layer providing additional functionality, such as a protective layer, a reflective layer, a wave plate, a viewing angle compensating film or a brightness-enhancing film, may be laminated onto the resulting polarizing film having a pressure-sensitive adhesive layer (adhesive polarizer).

The adhesive polarizer may be employed in all conventional liquid-crystal displays, without particular limitation as to the type of liquid-crystal panel. It is especially preferable for the adhesive polarizer of the invention to be part of a liquid-crystal display which includes a liquid-crystal panel obtained by attaching the adhesive polarizer to one or both sides of a liquid crystal cell in which liquid crystals are sealed between a pair of glass plates.

In addition to the above-described polarizing films, the pressure-sensitive adhesive of the invention can be used in other ways without limitation as to the application, such as in industrial sheets, particularly reflective sheets, structural adhesive sheets, adhesive sheets for photography, adhesive sheets for indicating traffic lines, optical adhesive products, and for electronic components. It can also be used in laminated products having a multilayer structure within areas of application where the operating concept is the same, such as adhesive sheet products for general commercial use, medical patches, and heat-activated uses.

The pressure-sensitive adhesive of the invention is a (meth)acrylic pressure-sensitive adhesive that includes an isocyanate group-containing silane coupling agent having a sulfur atom on a connecting chain. Because the initial adhesive strength when attached to glass, ITO or the like is low, it has excellent reworkability and the adhesive strength following wet heat treatment subsequent to attachment is sufficiently high, giving it excellent long-term durability.

EXAMPLES

The invention is illustrated more fully below by way of Working Examples and Comparative Examples, although these Examples are not intended to limit the invention. In the Examples, the viscosity, specific gravity and refractive index are values measured at 25° C. Also, GC is an abbreviation for gas chromatography and IR is an abbreviation for infrared absorption spectroscopy; the instrument used was a Thermo Scientific NICOLET 6700. NMR is an abbreviation for nuclear magnetic resonance spectroscopy; the instrument used was a Bruker AVANCE 400M. The viscosity was based on measurements taken at 25° C. with a capillary kinematic viscometer.

Working Example 1

Mercaptopropyltrimethoxysilane (980 g, 5 mol) and 2 g of 2,2'-azobis(2-methylbutyronitrile) were charged into a one-liter separable flask equipped with a stirrer, a reflux condenser, a dropping funnel and a thermometer, and heated to 90° C. Allyl isocyanate (415 g, 5 mol) was added dropwise thereto. Heat was generated by the reaction, and so the rate of addition was adjusted such as to keep the internal temperature from exceeding 95° C. Following the completion of dropwise addition, the flask contents were stirred for 1 hour under heating at 90° C. Upon confirming the disappearance of peaks from the mercaptopropyltrimethoxysilane starting material by GC measurement, the reaction was stopped. The resulting reaction product was a light-yellow liquid having a viscosity of 3.8 mm$^2$/s, a specific gravity of 1.10 and a refractive index of 1.464. Proton NMR measurement of this product showed it to be the isocyanate group-containing organosilicon compound of formula (6) below. The IR spectrum and ¹H-NMR spectrum of the reaction product are shown in FIGS. 1 and 2.

[Chemical Formula 36]

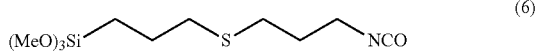
(6)

Working Examples 2 to 6

Aside from changing the mercaptopropyltrimethoxysilane used in Working Example 1 to other mercapto group-containing organosilicon compounds, corresponding isocyanate group-containing organosilicon compounds were obtained under the same reaction ratio and other conditions. The starting materials used and the products obtained are shown in Table 1.

Preparation of Polyurethane Elastomer for Adhesion Test

A polyurethane elastomer was obtained by mixing together 150 parts by weight of polyoxytetramethylene glycol having a number-average molecular weight of 1,000, 100 parts by weight of 1,6-xylene glycol, 0.5 part by weight of water, 200 parts by weight of hexamethylene diisocyanate and 800 parts by weight of dimethylformamide under stirring, heating the mixture to 90° C. and stirring in this state for 2 hours to effect the reaction, then adding 3 parts by weight of dibutylamine to stop the reaction and subsequently neutralizing the excess amount of amine with anhydrous acetic acid.

Primer Adhesion Test

Toluene solutions containing 10 wt % of the organosilicon compounds of the Working Examples and Comparative Examples were applied by brush as primers onto glass plates and dried for 5 minutes at 800, then cooled to room temperature (23° C.). In addition, a polyurethane elastomer was applied by brush and dried for 10 minutes at 100° C. The resulting applied film was scored at 1 mm intervals, both vertically and horizontally, to form a grid of 100 boxes, following which cellophane tape was pressed against the film and then peeled off. Adhesion between the urethane resin of the primer and the inorganic substrate was assessed based on the number of boxes that peeled off. In adhesion tests on the primers obtained in the Working Examples, there were no peeled boxes whatsoever for any of the substrates, indicating that the adhesion performance was outstanding. The results are shown in Table 3.

TABLE 1

| | Mercapto-group-containing organosilicon compound | Reaction product |
|---|---|---|
| Working Example 2 | (MeO)₂Si∼∼∼SH | (MeO)₂Si∼∼∼S∼∼∼NCO |
| Working Example 3 | (EtO)₃Si∼∼∼SH | (EtO)₃Si∼∼∼S∼∼∼NCO |
| Working Example 4 | (MeO)₃Si∼∼SH | (MeO)₃Si∼∼S∼∼∼NCO |
| Working Example 5 | (EtO)₃Si∼∼SH | (EtO)₃Si∼∼S∼∼∼NCO |
| Working Example 6 | (MeO)₃Si∼∼∼∼∼∼SH | (MeO)₃Si∼∼∼∼∼∼S∼∼∼NCO |

Working Examples 7 and 8

Aside from changing the allyl isocyanate used in Working Example 1 to other unsaturated carbon-carbon double bond-containing isocyanate compounds, corresponding isocyanate group-containing organosilicon compounds were obtained under the same reaction ratio and other conditions. The starting materials used and the products obtained are shown in Table 2. Also, the IR spectrum and ¹H-NMR spectrum for the product obtained in Working Example 7 are shown in FIGS. 3 and 4.

TABLE 2

| | Isocyanate compound | Reaction product |
|---|---|---|
| Working Example 7 | CH₂=CH-C(O)-O-CH₂CH₂-NCO | (MeO)₃Si∼∼∼S∼∼C(O)-O-CH₂CH₂-NCO |
| Working Example 8 | CH₂=C(CH₃)-C(O)-O-CH₂CH₂-NCO | (MeO)₃Si∼∼∼S-CH(CH₃)-C(O)-O-CH₂CH₂-NCO |

TABLE 3

| Substrate | Primer ingredient | Adhesiveness |
|---|---|---|
| Glass plate | Working Example 1 | 100/100 |
| | Working Example 2 | 100/100 |
| | Working Example 3 | 100/100 |
| | Working Example 4 | 100/100 |
| | Working Example 5 | 100/100 |
| | Working Example 6 | 100/100 |
| | Working Example 7 | 100/100 |
| | Working Example 8 | 100/100 |
| | primer not applied | 30/100 |
| | Comparative Example 1 | 50/100 |
| | Comparative Example 2 | 55/100 |

Comparative Example 1:
Isocyanatopropyltriethoxysilane

Comparative Example 2:
Isocyanatopropyltrimethoxysilane

Working Examples 9 to 16, Comparative Examples 3 to 7

Preparation of Acrylic Polymer for Pressure-Sensitive Adhesive Test

First, 98.1 g of n-butyl acrylate (BA), 0.6 g of 4-hydroxybutyl acrylate (4-HBA) and 1.3 g of 2-hydroxyethyl methacrylate (2-HEMA) were placed in a one-liter separable flask equipped with a stirrer, a reflux condenser, a dropping funnel and a thermometer, and these were dissolved by adding 100 g of ethyl acetate as the solvent. Nitrogen gas bubbling was then carried out for one hour to remove oxygen, the reaction system was nitrogen-purged and the temperature was held at 62° C. Next, 0.03 g of azobisisobutyronitrile was added as a polymerization initiator to the system under stirring and the reaction was effected for 8 hours at 62° C., thereby giving a (meth)acrylic copolymer as the acrylic polymer (base polymer).

Preparation of Pressure-Sensitive Adhesive

Pressure-sensitive adhesives for the respective Working Examples and Comparative Examples were prepared by mixing together, in the compounding formulations shown in Tables 4 and 5: 100 parts of (A) an acrylic polymer (the (meth)acrylic copolymer obtained above), (B) an adhesion modifier (the silane coupling agents obtained in Working Examples 1 to 8 or the organosilicon compounds of Comparative Examples 1 and 2), and (C) a crosslinking agent (trimethylolpropane tolylene diisocyanate adduct (TDI)).

TABLE 4

| Compounding formulation (pbw) | | Working Example | | | | | | | |
|---|---|---|---|---|---|---|---|---|---|
| | | 9 | 10 | 11 | 12 | 13 | 14 | 15 | 16 |
| (A) | | 100 | 100 | 100 | 100 | 100 | 100 | 100 | 100 |
| (B) | Working Example 1 | 0.1 | 0 | 0 | 0 | 0 | 0 | 0 | 0 |
| | Working Example 2 | 0 | 0.1 | 0 | 0 | 0 | 0 | 0 | 0 |
| | Working Example 3 | 0 | 0 | 0.1 | 0 | 0 | 0 | 0 | 0 |
| | Working Example 4 | 0 | 0 | 0 | 0.1 | 0 | 0 | 0 | 0 |
| | Working Example 5 | 0 | 0 | 0 | 0 | 0.1 | 0 | 0 | 0 |
| | Working Example 6 | 0 | 0 | 0 | 0 | 0 | 0.1 | 0 | 0 |
| | Working Example 7 | 0 | 0 | 0 | 0 | 0 | 0 | 0.1 | 0 |
| | Working Example 8 | 0 | 0 | 0 | 0 | 0 | 0 | 0 | 0.1 |
| (C) | TDI | 0.5 | 0.5 | 0.5 | 0.5 | 0.5 | 0.5 | 0.5 | 0.5 |

TABLE 5

| Compounding formulation (pbw) | | Comparative Example | | | | |
|---|---|---|---|---|---|---|
| | | 3 | 4 | 5 | 6 | 7 |
| (A) | | 100 | 100 | 100 | 100 | 100 |
| (B) | Working Example 1 | 0 | 0 | 0 | 0.0005 | 20 |
| | Comparative Example 1 | 0 | 0.1 | 0 | 0 | 0 |
| | Comparative Example 2 | 0 | 0 | 0.1 | 0 | 0 |
| (C) | TDI | 0.5 | 0.5 | 0.5 | 0.5 | 0.5 |

The resulting pressure-sensitive adhesives were coated onto a release liner and dried, after which a 25-μm uniform pressure-sensitive adhesive layer was obtained. The pressure-sensitive adhesive layer thus produced was attached to an iodine polarizer having a thickness of 185 μm, following which the resulting polarizer was cut to a suitable size and used in the various evaluations.

The polarizer test pieces thus produced were evaluated by the following evaluation test methods for durability/reliability, adhesive strength to glass, reworkability, and resistance to change in adhesive strength under hot or moist and hot conditions. The results are shown in Table 6.

Evaluation Tests

<Durability/Reliability>

Pressure-sensitive adhesive-coated polarizers (90 mm×170 mm) were attached to both sides of a glass substrate (110 mm×190 mm×0.7 mm) in a state where the optical absorption axes are orthogonally crossed. The pressure applied at this time was about 5 kgf/cm³ and the work was carried out in a clean room to keep bubbles and foreign matter from arising.

In order to evaluate the moisture and heat resistance properties of these test specimens, each specimen was left to stand 1,000 hours under conditions of 60° C. and 90% RH, following which the presence or absence of bubbles and peeling were checked. The heat resistance properties were evaluated by checking for bubbles and peeling after 1,000 hours of standing at 80° C. and 30% RH. Prior to evaluating the state of the test specimen, the specimen was left at rest for 24 hours at room temperature (23° C., 60% RH).

The following evaluation criteria were used to rate the durability.

Good: No bubbles and peeling
Fair: Slight bubbles and peeling
NG: Numerous bubbles and peeling <Adhesive Strength to Glass>

Pressure-sensitive adhesive-coated polarizers were aged for 7 days at room temperature (23° C., 60% RH), following which the polarizers were each cut into 1 inch×6 inch sizes and attached to 0.7 mm thick alkali-free glass using a 2 kg rubber roller. The specimen was held for 1 hour at room temperature, following which the initial adhesive strength was measured. The specimen was then aged for 4 hours at 50° C. and subsequently held for 1 hour at room temperature, after which the adhesive strength was measured.

<Reworkability>

Pressure-sensitive adhesive-coated polarizers (90 mm×170 mm) were attached to a glass substrate (110 mm×190 mm×0.7 mm), following which the specimen was left to stand for 1 hour at room temperature (23° C., 60% RH) and subsequently aged for 4 hours at 50° C. The specimen was allowed to cool for 1 hour at room temperature, after which the polarizer was peeled from the glass.

The reworkability was assessed as follows based on whether or not peeling was possible without destroying the polarizer or the glass plate and without leaving pressure-sensitive adhesive on the glass surface.

Good: Easily re-peelable
Fair: Re-peeling is somewhat difficult (pressure-sensitive adhesive remains on glass surface)
NG: Cannot be peeled; glass or polarizer fails

TABLE 6

|  |  | Adhesive strength to glass (gf/in) | | Durability/Reliability | |  |
| --- | --- | --- | --- | --- | --- | --- |
|  |  |  |  | 1,000 hrs | 1,000 hrs |  |
|  |  | Initial adhesive strength | After 4 hrs at 50° C. | at 60° C., 90% RH | at 80° C., 30% RH | Reworkability |
| Working Example | 9 | 350 | 1,250 | good | good | good |
|  | 10 | 360 | 1,280 | good | good | good |
|  | 11 | 330 | 1,380 | good | good | good |
|  | 12 | 310 | 1,290 | good | good | good |
|  | 13 | 370 | 1,340 | good | good | good |
|  | 14 | 360 | 1,300 | good | good | good |
|  | 15 | 380 | 1,410 | good | good | good |
|  | 16 | 350 | 1,320 | good | good | good |
| Comparative Example | 3 | 200 | 200 | NG | NG | good |
|  | 4 | 320 | 350 | fair | fair | NG |
|  | 5 | 330 | 400 | fair | fair | NG |
|  | 6 | 210 | 220 | NG | NG | good |
|  | 7 | 780 | 1,530 | good | good | NG |

Comparative Example 3 did not include an adhesion modifier, and sufficient adhesiveness did not appear after thermal curing. Comparative Examples 4 and 5 are cases in which isocyanatopropyl group-containing silane coupling agents according to the existing art were used. The isocyanate group-to-silyl connecting chain in these compounds was a propylene group; because of the low hydrophobicity of the overall molecule, initial adhesive force reworkability does appear, but affinity with the resin was relatively inadequate, and so the ultimate bonding strength following the cure was not sufficient. In Comparative Example 6, too little component (B) was used, and so the effects were inadequate. On the other hand, in Comparative Example 6, too much component (B) was used, as a result of which excessive adhesion appeared from the start and the reworkability was inadequate.

It is apparent from the above results that the inventive pressure-sensitive adhesive has an excellent initial reworkability, exhibits a sufficient adhesive strength with glass when high-temperature or high-temperature and high-humidity treated, and has an excellent long-term durability.

The invention claimed is:

1. An isocyanate group-containing organosilicon compound of formula (1) below

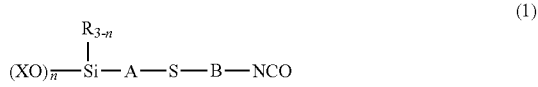

wherein X is a monovalent hydrocarbon group of 1 to 4 carbon atoms, R is a monovalent hydrocarbon group of 1 to 6 carbon atoms, A is a divalent hydrocarbon group of 1 to 10 carbon atoms, B is a divalent hydrocarbon group of 2 to 10 carbon atoms that is bonded through an ester group, and n is an integer from 1 to 3.

2. The isocyanate group-containing organosilicon compound of claim 1 which has formula (3) below

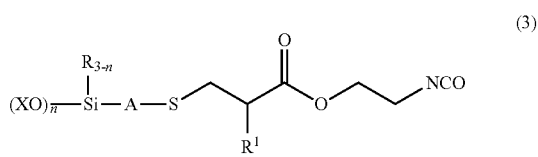

wherein X, R, A and n are as defined above, and $R^1$ is a hydrogen atom or a methyl group.

3. The isocyanate group-containing organosilicon compound of claim 2 wherein $R^1$ is a hydrogen atom.

4. A bonding agent containing the isocyanate group-containing organosilicon compound of claim 1.

5. A coating agent containing the isocyanate group-containing organosilicon compound of claim 1.

6. An article obtained by coating or surface treating a substrate with the coating agent of claim 5.

7. The article of claim 6, wherein the substrate that is coated or surface-treated with the coating agent is a glass fiber product selected from among glass cloth, glass tape, glass mat and glass paper.

8. The article of claim 6, wherein the substrate that is coated or surface-treated with the coating agent is an inorganic filler.

9. The article of claim 6, wherein the substrate that is coated or surface-treated with the coating agent is ceramic or metal.

10. A method for preparing the isocyanate group-containing organosilicon compound of claim 1, which method comprises the step of thiol-ene addition reacting (i) a mercapto group-containing organosilicon compound of general formula (4) below

[Chemical Formula 2]

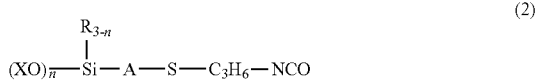
(2)

wherein X, R, A and n are as defined above with (ii) an unsaturated double bond-containing isocyanate compound of general formula (5) below

Z—NCO  (5)

wherein Z is an unsaturated double bond-containing monovalent hydrocarbon group of 2 to 10 carbon atoms that is bonded through an ester group in the presence of a radical generator.

11. A pressure-sensitive adhesive containing the isocyanate group-containing organosilicon compound of claim 1, which pressure-sensitive adhesive comprises:

(A) 100 parts by weight of an alcoholic hydroxyl group-containing acrylic polymer,
(B) from 0.001 to 10 parts by weight of the isocyanate group-containing organosilicon compound, and
(C) from 0.01 to 10 parts by weight of a polyfunctional crosslinking agent.

12. An adhesive polarizer comprising a polarizing film and an adhesive layer formed on one or both sides of the polarizing film using the pressure-sensitive adhesive of claim 11.

13. A liquid crystal display comprising a liquid crystal panel that comprises a liquid crystal cell wherein liquid crystals are sealed between a pair of glass plates and, attached to one or both sides of the liquid crystal cell, the adhesive polarizer of claim 12.

* * * * *